(12) United States Patent
Yeik et al.

(10) Patent No.: US 7,492,987 B2
(45) Date of Patent: Feb. 17, 2009

(54) FIBER OPTIC LASER ENERGY DELIVERY DEVICES

(75) Inventors: Glenn D. Yeik, Lake Forest, CA (US); L. Dean Crawford, Irvine, CA (US)

(73) Assignee: Trimedyne, Inc., Lake Forest, CA (US)

( * ) Notice: Subject to any disclaimer, the term of this patent is extended or adjusted under 35 U.S.C. 154(b) by 0 days.

(21) Appl. No.: 11/641,155

(22) Filed: Dec. 19, 2006

(65) Prior Publication Data

US 2007/0179485 A1    Aug. 2, 2007

Related U.S. Application Data

(60) Provisional application No. 60/751,692, filed on Dec. 19, 2005.

(51) Int. Cl.
*G02B 6/26* (2006.01)
*A61B 18/18* (2006.01)

(52) U.S. Cl. .................. 385/31; 606/4; 606/15
(58) Field of Classification Search ........................ None
See application file for complete search history.

(56) References Cited

U.S. PATENT DOCUMENTS 6,027,627 A * 2/2000 Li et al. ................ 204/603
2006/0184162 A1* 8/2006 Smith ........................ 606/4

* cited by examiner

*Primary Examiner*—Tina M Wong
(74) *Attorney, Agent, or Firm*—Olson & Cepuritis, Ltd.

(57) ABSTRACT

Improved laser energy delivery devices, providing greater transmission efficiency, longevity of use and safety are described. In one embodiment, a device for delivering laser energy includes a conventional optical fiber within a metal or plastic cannula provided with a laser energy emission window. A reflective material is disposed in a space between the distal end portion of a metal or plastic sheath and the optical fiber, as well as about any extension or endpiece of the distal end of the sheath. The reflective material reflects aberrant emissions of laser energy from the optical fiber as it erodes, and laser energy backscattered from the target tissue away from the distal end of the sheath back into the optical fiber or out of the distal end of the sheath, thereby preventing damage due to overheating. Other embodiments include devices that transmit laser energy more safely, efficiently and durably laterally from the axis of the optical fiber.

24 Claims, 7 Drawing Sheets

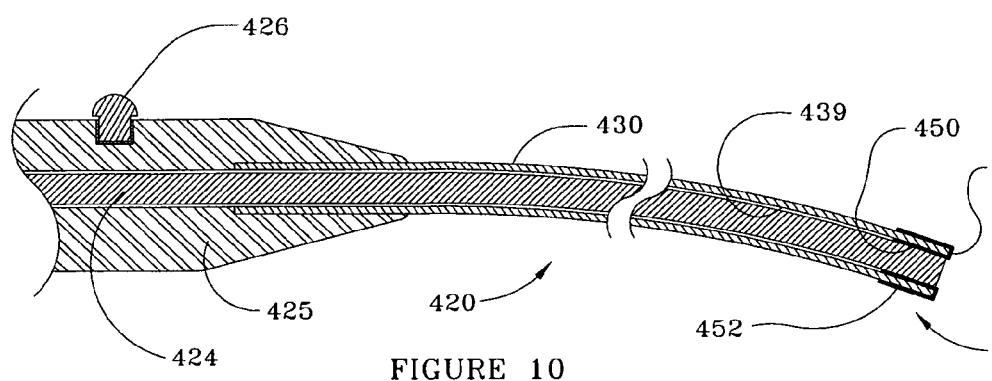
FIGURE 10
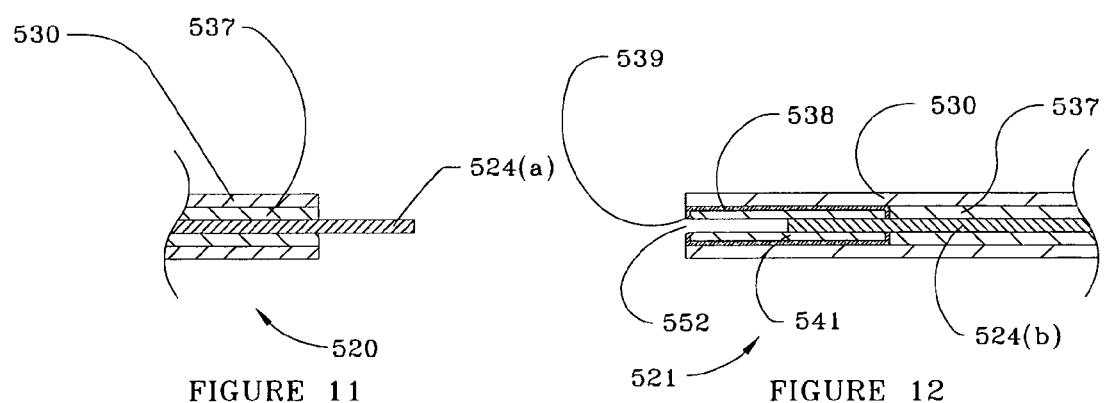
FIGURE 11
FIGURE 12

FIBER OPTIC LASER ENERGY DELIVERY DEVICES

CROSS-REFERENCE TO RELATED APPLICATIONS

This application claims benefit of U.S. Ser. No. 60/751,692 filed on Dec. 19, 2005.

FIELD OF THE INVENTION

The present invention relates to improved fiber-optic laser energy delivery devices, which are safer and have higher delivery efficiency, greater durability and a longer useful life than conventional fiber-optic laser energy delivery devices.

BACKGROUND OF THE INVENTION

For use in certain medical applications, such as laser arthroscopy, in which an optical fiber conveying laser energy from a laser is introduced through a tiny puncture into the knee, shoulder, hip, ankle, elbow or other joint to treat damage or disease in the joint, the optical fiber is disposed within a metal tube or cannula, usually made of surgical grade stainless steel. The distal end of the optical fiber is usually positioned at or just within the distal end of the metal cannula.

In use, due to back-scatter of light energy from the target tissue, particularly if a dense material, such as bone, is being exposed to laser energy, the protective buffer coating and cladding of the optical fiber can be destroyed and the optical fiber itself can be eroded. Laser energy can escape from the side walls of an eroded optical fiber in an undesired direction and, as the optical fiber is eroded further back into the metal cannula, energy is emitted at aberrant angles from the deformed distal end of the optical fiber, which can strike the distal end portion of the metal cannula. At energy levels sufficient to vaporize cartilage or bone, when struck by such aberrant beams of laser energy, the metal cannula becomes hot and can emit sparks as the metal is vaporized. The deposition of tiny bits of metal in the body can cause adverse effects.

Electropolishing the interior of the distal end of the metal cannula may not prevent laser energy from damaging the metal cannula. As a result, the laser energy delivery device is usually discarded as soon as sparks are seen, adding to the cost of the procedure.

When the distal end of one optical fiber is juxtaposed to the proximal end of another optical fiber, laser energy that misses the core of the proximal end of the other fiber can cause overheating at the juncture. Likewise, laser energy that misses the core of the proximal end of an optical fiber encased in a laser connector can erode the optical fiber, overheat the connector and be reflected back into the laser. In both of the above examples, injury to the operator or the laser can occur, as well as premature failure of the device.

When laser energy must be delivered laterally from the axis of an optical fiber at an angle of about 60° or more, an optical fiber cannot be bent at such an angle in a confined space, as it will leak laser energy if the bend radius thereof exceeds a certain limit (about a 1 cm radius for an optical fiber with a core diameter of 200 microns). For use in a confined space, such as in tissue, or in a duct, blood vessel, hollow organ or surgically created passageway, a side-firing, fiber optic laser device, emitting energy at a 60° or greater angle from the axis of the device, is preferred.

As shown in co-owned U.S. Pat. Nos. 5,649,924; 5,437,660 and 5,242,438, the disclosures of which are fully incorporated herein by reference, a reflective metal surface, such as gold, silver, copper or a dielectric may be positioned opposite the distal end of a straight-ahead firing optical fiber to reflect laser energy at an angle of about 70° to 100° by positioning the metal surface at an angle of about 35° to 50°, respectively, from the axis of the optical fiber. Such devices can be made of medical grade stainless steel or other metal which has been plated with gold, silver, copper or other reflective material, may contain an insert of such a reflective material or can be composed entirely of the reflective material. Silver is preferred as it is almost as reflective as gold, costs less than gold and does not oxidize like copper.

Such devices are particularly well suited to the lateral reflection of wavelengths of laser energy at 300 to 1600 nm, such as from excimer, argon, KTP, diode, Nd:YAG and other lasers in an aqueous liquid medium, as such wavelengths are not highly absorbed by water.

Another solution is to bevel the distal end of an optical fiber at an angle of about 30° to 50°, preferably about 35° to 40°, most preferably at about 39° from the axis of the optical fiber, into a prism-like shape. Encasing the beveled distal end of the optical fiber inside a quartz or fused silica, closed-ended capillary tube provides the air interface opposite the beveled surface of the optical fiber which is required for total internal reflection of the laser energy to occur laterally from the axis of the optical fiber. To prevent mechanical damage to the capillary tube, the distal end portion of the beveled optical fiber and the surrounding capillary tube are preferably encased in a metal cannula, such as medical grade stainless steel.

However, back-scatter of laser energy from the target tissue and imperfections in the beveled surface of the optical fiber and the surrounding capillary tube, as well as the curvature of the capillary tube, can cause some of the energy to be emitted in other than the desired direction, which can erode the capillary tube and cause it to fracture or fail to maintain the needed air environment. Such aberrant laser energy can also overheat the non-energy emitting, back surface or sides of the capillary tube or metal cannula.

When such devices are used in industrial, scientific or military applications close to sensitive materials, or in medical applications, where sensitive structures such as nerves or blood vessels may be inadvertently struck by laser energy, even a small amount of laser energy emitted in other than the intended direction may pose an unacceptable risk. Also, a delicate industrial material or a sensitive bodily structure, such as a nerve, blood vessel or other tissue, may be damaged by contact with an overheated metal or glass portion of the device.

It is an object of the present invention to improve the laser energy delivering efficiency, reduce overheating and increase the useful life of devices that utilize an optical fiber whose distal end has been beveled at an angle of about 30° to 50° and encased in a closed-ended capillary tube to obtain the benefit of total internal reflection of laser energy of wavelengths of about 300 to 3000 nm at an angle of about 60° to 90° from the axis of the optical fiber. (See FIGS. 1-5.)

It is an object of the present invention to improve the laser energy delivery efficiency, reduce overheating and increase the useful lifetime of devices that use a reflective metal surface, inclined at an angle of about 35° to 50° opposite the distal end of an optical fiber to reflect laser energy of wavelengths of about 300 to 1400 nm at an angle of about 70° to 100° from the axis of the optical fiber. (See FIGS. 14 and 15.)

It is an object of the present invention to improve the laser energy delivery efficiency, reduce overheating and increase the useful lifetime of devices that use a reflective metal surface, inclined at an angle of about 35° to 50° opposite the distal end of an optical fiber, with a window to exclude aqueous liquids to reflect laser energy at wavelengths of about 1400 to 3000 nm at an angle of about 70° to 100° from the axis of the optical fiber. (See FIGS. 17, 18, 19a) and 19(b).)

It is an object of the present invention to avoid erosion from back-scattered laser energy, aberrant emissions of laser energy and a loss of laser energy delivery efficiency from the distal end of an optical fiber or a device in which the distal end of an optical fiber whose distal end has been beveled at an angle of about 30° to 50° and encased in a closed-ended capillary tube to obtain total internal reflection of the laser energy, using laser energy of wavelengths of about 300 to 3000 nm. (See FIGS. 16(a)-(d)).

It is an object of the present invention to improve laser energy delivery efficiency, reduce overheating and increase the useful lifetime of devices in which an optical fiber is encased in a metal or plastic cannula, using laser energy at wavelengths of about 300 to 3000 nm. (See FIGS. 6-10.)

It is an object of the present invention to improve laser energy delivery efficiency, reduce overheating and increase the useful lifetimes of devices in which the distal end of one optical fiber is juxtaposed opposite the proximal end of another optical fiber inside a metal or plastic sheath for transmission of laser energy of wavelengths of about 300 to 3000 nm. (See FIGS. 11 and 12.)

It is an object of the present invention to improve laser energy transmission efficiency, reduce overheating and increase the useful lifetimes of devices in which the proximal end of an optical fiber is contained in a connector for optically coupling the optical fiber to a source of laser energy of wavelengths of about 300 to 3000 nm, as well as to avoid the reflection of laser energy back into the source of laser energy. (See FIG. 13.)

The present invention addresses and satisfies all of the foregoing objects.

SUMMARY OF THE INVENTION

An improved laser device is provided with a laser energy conduit having a proximal end portion for coupling to the laser energy source and a distal end from which laser energy can be emitted. The proximal end of the conduit is adapted for coupling to a laser energy source, and a hollow sheath surrounds the distal end of the conduit. The hollow sheath defines a window through which laser energy emitted from the distal end of the conduit passes. A reflective material is positioned between the laser energy conduit and the hollow sheath for reflecting stray laser energy that is emitted from the laser energy conduit. Preferably the port is situated so that reflected laser energy is also emitted through the port.

In a preferred embodiment a transparent capillary tube, such as a quartz or fused silica sleeve, is provided within the hollow sheath and positioned over a distal end portion of the laser energy conduit. The reflective material can be provided, e.g., by coating, on the outer surface of the capillary tube.

The present improvement can be embodied in devices that emit laser energy straight ahead or at an angle of up to about 60° from the axis of the optical fiber, as well as at an angle of about 60° to 100° from the axis of the optical fiber in a space too confined to permit an optical fiber to be bent at an angle sufficient to achieve such effect.

The improved devices embodying the present invention can be used externally on the body of a human or animal, interstitially within tissues, on surgically exposed tissues, in a hollow organ or body cavity or in a duct, blood vessel or surgically created passageway, as well as in industrial, scientific or military applications. Devices embodying the present invention can also be employed to prevent over-heating and damage to devices in which the proximal end of an optical fiber is encased in a connector and optically coupled to a source of laser energy, as well as when the distal end of one optical fiber is juxtaposed to the proximal end of another.

BRIEF DESCRIPTION OF THE DRAWINGS

FIG. 10 is partial, vertical cross-sectional, side view of the distal end portion of an alternate embodiment of the device of FIG. 6;

FIG. 11 is a partial, vertical cross-sectional, side view of an alternative sheath embodiment of the device of the present invention;

FIG. 12 is a partial, vertical cross-sectional, side view of the mating sheath section for the sheath shown in FIG. 11;

DETAILED DESCRIPTION OF THE PREFERRED EMBODIMENTS

Figure 1:
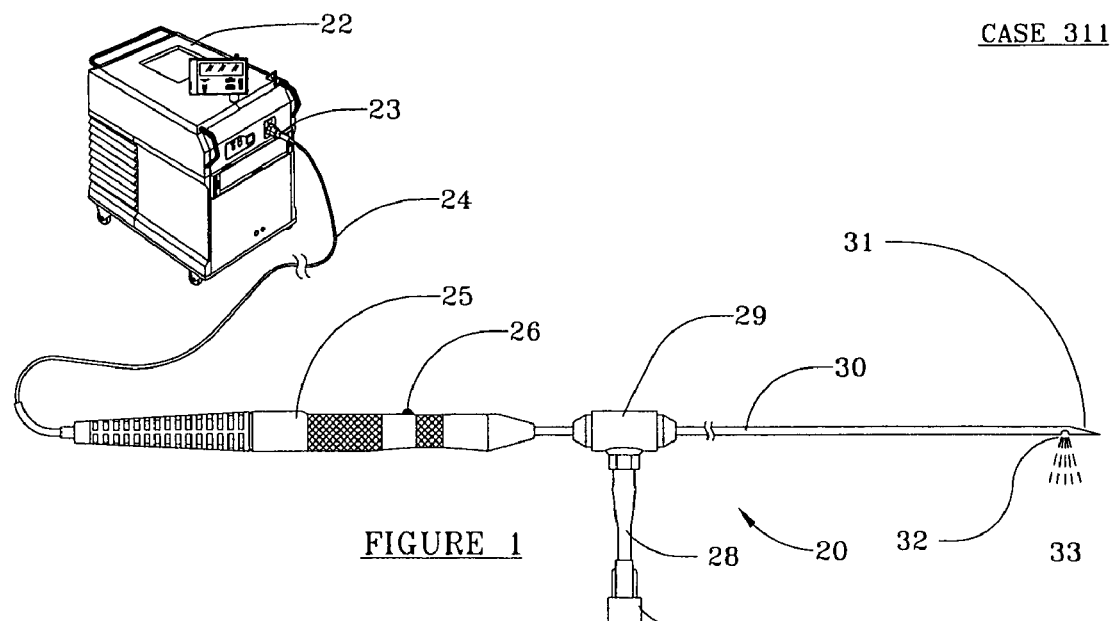
FIG. 1 is an exterior, partially enlarged, side elevational view of the device of the present invention.

While this invention is susceptible of embodiment in many different forms, there are shown in the drawings and will be described in detail herein specific embodiments thereof, with the understanding that the present disclosure is to be considered as an exemplification of the principles of the invention and is not to be limited to the specific embodiments illustrated.

A source of laser energy of wavelengths of from about 300 to 3000 microns may be optically coupled to an optical fiber. Ordinary quartz or fused silica optical fibers may be used, for example, with argon, KTP, diode, Alexandrite, Neodymium: YAG, Alexandrite and other lasers emitting at wavelengths of about 300 to 1400 nanometers. Optical fibers with a high hydroxyl content, called "high OH" optical fibers, must be used, for example, with excimer (excited dimer) lasers, emitting at wavelengths of 300 to 400 nanometers. Optical fibers with a low hydroxyl content, called "low OH" optical fibers, must be used, for example, with Holmium:YAG lasers and other lasers emitting energy at wavelengths of about 1800 to 2500 nanometers. Ultra low-OH fibers can be used with lasers emitting at wavelengths from 2500 to 3000 nm, including Erbium lasers emitting at 2940 nm. Such optical fibers are manufactured by OFC Fitel of Avon, Conn. and others.

Erbium laser energy and laser energy at wavelengths of from about 3000 to 11000 nanometers, for example, such as carbon monoxide or carbon dioxide laser energy, emitted at wavelengths of about 2,940, 6000 or 10,600 nanometers, respectively, can be delivered through a series of mirrors attached to an articulated arm for surface operation. If internal use of such wavelengths is desired, a short length of an optical fiber of a special composition, such as sapphire, zirconium fluoride (ZrF4), chalcogenide (As2S3) or others, as known in the art, may be attached to the distal end of the articulated arm.

Alternatively, a hollow waveguide, as known in the art, may be attached to the distal end of a mirror bearing articulated arm and, if desired, a short length of optical fiber made of one of the special compositions described above may also be fixedly disposed within and extend somewhat beyond the distal end of the hollow waveguide. For simplicity, all references herein to an "optical fiber" shall also apply to an articulated arm/mirror system, an articulated arm/mirror system with an attached special composition optical fiber, a hollow waveguide or a hollow waveguide from whose distal end a special composition optical fiber extends.

In certain medical applications for example, in arthroscopy, a metal cannula may be disposed over the optical fiber to protect it from damage or breakage. To prevent erosion of the optical fiber and damage to the metal cannula in which the optical fiber may be disposed from the back-scatter of laser energy from the target tissue, about 1 cm to 3 cm of the distal end of the metal cannula can be electroplated with gold, silver, copper or other reflective material. The thickness of the plating should be at least about 3 to 10 thousandths of an inch, preferably about 5 to 6 thousandths of an inch thick to avoid erosion during use. While the plating will reflect laser energy back-scattered toward the metal cannula from the target tissue, if the interior surface of the metal cannula is not uniformly plated, back-scattered laser energy from the target tissue can erode the buffer coating and cladding of the optical fiber and the optical fiber itself, causing laser energy to be emitted in aberrant directions, damaging the metal cannula.

If the inside diameter of the distal end of the metal cannula is small, such as 1.5 mm or less, it is difficult to assure that a uniform plating of the desired thickness can be deposited on the interior surface of the metal cannula. While polished stainless steel or aluminum are reflective, they are not as good reflectors as gold, silver, copper or a dielectric, they absorb energy and can melt, and are not as durable in use.

In a preferred embodiment, a reflective material, such as a strip of gold, silver or copper, and the likes, preferably silver for the reasons discussed above, about 1 cm to 3 cm in length, is formed into a hollow tube and attached by an adhesive to the interior surface of the distal end of the metal cannula. The strip of reflective metal should be at least about 3 to 10 thousandths of an inch thick, preferably at least about 5 to 6 thousandths of an inch thick, as a reflective metal strip of a lesser thickness can be eroded in normal usage. For use with a Holmium:YAG laser, silver or gold are preferred, and silver is most preferred as it reflects laser energy almost as well as gold, is much less expensive than gold and does not oxidize like copper.

The reflective material within the distal end of the metal cannula reflects laser energy leaking from the cladding or eroded optical fiber away from the metal cannula, as well as any laser energy which enters the cannula, as a result of back-scatter of laser energy from the target tissue.

In laboratory testing, when 80 watts of Holmium laser energy (3.07 joules per pulse at a pulse repetition rate of 26 Hz) was emitted in water against beef heart tissue from a metal cannula containing a low OH optical fiber with a core diameter of 550 microns, the metal cannula without a reflective metal strip within its distal end was destroyed after eighteen minutes of lasing, whereas an identical metal cannula with a silver metal strip within its distal end survived lasing for one hour without significant damage, and was still functional.

To avoid damage to the exterior, distal end portion of the metal cannula from laser energy back-scattered from the target tissue, the reflective metal strip can also extend about 1 to 3 cm over the exterior of the distal end portion of the cannula.

To achieve the lateral emission of laser energy at an angle of about 70° to 90° from the axis of an optical fiber, alternatively, the distal end of an optical fiber can be beveled at an angle of about 35° to 45° from the axis of the optical fiber, preferably about 39°, and the distal end of the optical fiber can be encased in a closed-ended transparent capillary tube, e.g., a quartz or fused silica capillary tube, to maintain an air environment about the beveled distal end of the optical fiber, so as to provide total internal reflection of the light energy.

If, after removal of the buffer coat and any polymer cladding from the distal end portion of the optical fiber, the entire capillary tube is fused to the glass cladding of the optical fiber or to the optical fiber itself, thermal stress to the capillary tube and optical fiber may occur from the application of sufficient heat to fuse the entire capillary tube to the optical fiber or its glass cladding. Preferably, a portion of the distal end of the capillary tube, particularly the portion through which laser energy will be transmitted from the beveled surface of the optical fiber, after removal of the optical fiber's buffer coating and any polymer cladding, may be thermally fused to the glass cladding of the optical fiber or the optical fiber, itself. The proximal end portion of the capillary tube may be attached by an adhesive, glue or epoxy to the buffer coating of the optical fiber or, with the buffer coating and any polymer cladding removed, may be attached by an adhesive, glue or epoxy to the glass cladding of the optical fiber or the optical fiber, itself.

In any case, the capillary tube should be made of a material substantially transparent to the wavelength of light being used (i.e. with an appropriate low-OH or high-OH content, as described above) for the wavelength of laser energy being used, just as the OH content of the optical fiber is based on the wavelength of light being transmitted.

A handpiece to facilitate handling of the optical fiber may be disposed about 5 to 50 cm, preferably about 10 to 40 cm, from the distal end of the optical fiber. A plastic or metal tubular sheath, whose inside diameter is just a bit larger than the outside diameter of the optical fiber, is employed to protect and stabilize the optical fiber. Such a sheath may extend over the optical fiber from within the distal end of the handpiece to the proximal end of the capillary tube encasing the beveled distal end of the optical fiber or to a point about 0.2 to 0.5 cm proximal from the proximal end of the sheath. The metal sleeve, with a port for emission of the laser energy opposite the beveled optical fiber, covers the closed-ended capillary tube and beveled optical fiber to protect them from mechanical damage.

The sheath is preferably made of a rigid plastic, such as PEEK (poly ethyl ethyl keytone) or a metal, such as surgical grade stainless steel, if a wavelength of laser energy which is highly absorbed by aqueous liquids (i.e. greater than about 1400 nm) is to be used, as such liquids are quickly turned to steam, causing the formation of a bubble. When the bubble expands and collapses with each pulse of laser energy, the expansion of the gas bubble and the acoustic shockwave upon the bubble's collapse can cause the distal end portion of the device to rapidly move back and forth. A metal or suitably stiff plastic sheath can reduce or eliminate vibration of the distal end of the device, enabling its position opposite the target tissue to be more easily maintained.

The tubular metal sheath described above can also extend over the closed-ended capillary tube, with a port for emission of laser energy opposite the beveled distal end surface of the optical fiber and, if desired, it can extend a relatively short distance over the optical fiber, about 0.2 to 0.5 cm of the portion of the optical fiber extending proximally from the capillary tube. The distal end of the sheath may be blunt or formed into a point or syringe needle-like shape.

In addition to protecting the fragile, closed-ended capillary tube from mechanical damage, if the capillary tube shatters, the sheath prevents the fragments of the capillary tube from lodging in the target tissue or being carried elsewhere.

The metal sleeve extending over the closed-ended capillary tube may be made of medical grade stainless steel, aluminum or other metal which has been gold or silver plated to a depth of 3 to 10 thousandths, preferably at least 5 to 6 thousandths of an inch, to prevent damage to the sheath from aberrant emissions of laser energy from the capillary tube or an eroded optical fiber, as described above. However, as it may be difficult to assure that the interior of the sleeve, particularly if its inside diameter is less than 1.5 mm, has been uniformly gold or silver plated, a tube consisting of a thin sheet of gold, silver, copper or other reflective material can be disposed within the metal sleeve, except for about 160° to 40° of the interior thereof, preferably, except for about 120° to 60° thereof, in line with the laser energy emission port. To prevent damage to the distal, exterior of the metal sheath, a thin sheet of such a reflective material may be attached to the distal 1 to 3 cm of the exterior of the metal sleeve, but not over the laser energy emission port.

Alternatively, the entire metal sheath is made of gold, silver, copper or other reflective material, preferably silver for its lower cost than gold and almost equal reflectivity and avoiding the oxidation which can cause copper to lose its reflectivity. Very pure gold or silver is preferable for the reflective metal strip or entire reflective metal sleeve, as contaminants can reduce the metal's reflectivity and its durability.

The cost of making the metal sheath entirely of a highly reflective material, such as gold, silver or copper, which are easy to mill or machine, is offset by the higher cost of milling or machining the sheath from medical grade stainless steel, with the extra cost of (a) plating or coating the interior and exterior of a stainless steel tip or sleeve with gold, silver, copper or a dielectric of an appropriate thickness, as described above, or (b) attaching an insert of gold, silver, copper or a dielectric of an appropriate thickness, as described above, to a properly inclined surface, as described above, within the emission port of a stainless steel sheath and attaching a sheet of such a highly reflective material to its exterior.

The distal end of the sheath may be joined to the proximal end of the metal sheath by crimping, an adhesive or matching threaded surfaces, or by a combination of the above means, and the two can be joined in a manner providing for fluid communication, as known in the art.

An optional infusion port near the proximal end of the tubular sheath or in the handpiece, communicating with the interior of the sheath and optional metal sleeve, enables a fluid, such as water or saline, or a gas such as air, $CO_2$ or other biocompatible gas, to be infused into the space between the inner surface of the sheath and sleeve and the exterior of the capillary tube and optical fiber assembly to cool the distal end of the sheath and sleeve and the capillary tube and optical fiber assembly, as well as to flush debris therefrom. The fluid may exit through the laser energy emission port in the sleeve or any other provided port or ports in the sheath.

If a tube made of a thin sheet of a reflective material is disposed within the interior of the metal sheath, surrounds about 200° to 330° of the exterior of the capillary tube, preferably about 240° to 300° of its exterior, leaving the laser energy emission port in the sheath unobstructed. If a tubular reflective metal strip is attached to the exterior of the distal end of the metal sheath, it may extend over the entire distal surface, with a cut-out matching the laser energy emission port.

In a preferred embodiment, where the device is intended to function as a laser needle or probe, a metal sheath may extend distally from within the handpiece over the optical fiber and the closed-ended capillary tube. The metal sheath can terminate in a blunt, rounded, pointed or syringe shaped tip at the distal end thereof. A thin, tubular strip of gold, silver, copper or other reflective material, preferably silver for the reasons set forth above, about 1 to 3 cm in length, is attached with an adhesive or the like to the interior surface of the distal end of the sheath, extending over about 200° to 330° of the non-emitting surface of the capillary tube, preferably about 240° to 300° thereof, without obstructing the laser emission area of the capillary tube or the energy emission port of the sheath. Likewise, to protect the exterior of the distal end of the optional metal sheath, the strip of reflective material may extend about 1 to 3 cm of the exterior of the distal end of the sheath, with a cut-out matching the laser energy emission port.

Preferably, one of the reflective metal strips also extends over the distal end face of the sheath to protect it from stray laser energy or energy back-scattered from the target tissue. Since gold, silver and copper are malleable, if desired, one reflective metal strip can be formed onto and attached by an adhesive or the like to all three surfaces of the sheath.

The strips of reflective material described above reflect aberrant beams of laser energy from imperfections in the optical fiber, its beveled distal end or the capillary tube and reflect laser energy back-scattered from the target tissue away from the capillary tube, the optical fiber and its beveled surface and the metal sheath. The reflected laser energy that exits the emission port, may avoid overheating of the sides and non-energy emitting (back) surface of the metal sheath and increase the device's energy transmission efficiency and longevity.

An additional, surprising benefit of the reflective metal strip of the preferred embodiment is a further improvement in the device's durability and longevity. Since the reflective metal strip inside the metal sheath fills almost all or a significant portion of the space between the exterior of the non-laser energy emitting portion of the capillary tube and the interior of the metal sheath, except for the portion in line with the laser emission port, it leaves an open fluid pathway over the laser energy emitting surface of the capillary tube and the emission port of the sheath.

When a liquid, such as saline or water, is infused into the metal sheath, a greater volume of the liquid is channeled through the open fluid pathway over the energy emitting portion of the capillary tube than would occur if the liquid flowed completely around the capillary tube. This cools both the energy emitting surface of the capillary tube and the energy emitting portion of the sleeve or sheath, and flushes debris away from the energy emitting surface of the capillary tube and the emission port of the metal sheath, avoiding contamination and resultant damage to the capillary tube and metal sleeve or sheath.

Testing demonstrated that the longevity of such a side firing, laser energy delivery device was substantially increased when a strip of reflective material was disposed therein as described above. When 40 watts of Holmium laser energy (2 joules per pulse at a repetition rate of 20 hertz) was transmitted into such devices with and without a reflective silver strip, the devices with the reflective silver strip survived for an average of 49.5 minutes, whereas the devices without the reflective silver strip survived for an average of only 13 minutes.

In addition, to prevent back-scattered laser energy being transmitted backwards through the capillary tube, a ring or washer-shaped hollow disc or strip of a reflective metal can be placed over the proximal end face of the capillary tube to prevent damage to the metal sheath surrounding the proximal end of the capillary tube and the buffer coating and cladding of the optical fiber.

In medical applications, since a side-firing, laser energy delivery device may be positioned between a nerve, blood vessel or other delicate tissue and fired away from the nerve, blood vessel or delicate tissue toward a targeted tissue, for example, such as a tumor or a portion of the nucleus pulposa extruded from a ruptured disc, it would be desirable to avoid overheating of the non-energy emitting (back) surface of the device.

In testing, when laser energy at 10 watts (1 joule per pulse at a repetition rate of 10 hertz) was emitted for 5 seconds into side-firing, laser energy delivery devices constructed as described above, with and without a reflective silver strip, in air, the temperature of the (back) non-energy emitting surface of the devices with a reflective silver strip increased from an average of 20° C. to an average of 45° C., whereas the temperature of the (back) non-energy emitting surface of identical devices without a reflective silver strip rose from an average of 20° C. to an average of 192° C.

Alternatively, where a plastic or metal sheath extends over an optical fiber and the capillary tube encasing the beveled, distal end portion of the optical fiber, for example, in a device designed for vaporization of a portion of an enlarged prostate to restore urine flow to normal levels, the metal sheath may be made of two or more components for ease of assembly. If the metal sheath is made of two or more components, they are preferably of the same material to avoid different coefficients of expansion causing a loosening of their attachment to each other.

In an alternative means for causing the emission of laser energy at an angle of about 70° or more from the axis of an optical fiber, for the transmission of laser energy at wavelengths of about 300 to 1400 nm, including excimer, Argon, KTP, diode, Nd:YAG and other lasers, instead of the distal end of the optical fiber being beveled and enclosed in a closed-ended capillary tube, the distal end face of the optical fiber can be flat, emitting laser-energy forwardly, and the distal end portion of the optical fiber can be enclosed in a metal sleeve or tip made of a metal, such as surgical grade stainless steel, which has been plated with gold, silver, copper, a dielectric or other reflective material of the thickness described above. Alternatively, an insert of such a reflective material may be attached within the distal end of the metal sheath, or the entire metal sheath can be made of such a reflective material.

In the alternate embodiment described above, the reflective surface opposite the distal end of the optical fiber is inclined at an angle of about 40° to 50°, preferably about 45°, from the axis of the optical fiber. The distal end of the optical fiber can extend into a cavity in the metal sheath, defining the port for emission of the laser energy, and the inclined surface described above. Laser energy emitted from the optical fiber is reflected from a 45° inclined reflective surface at an angle of about 90° from the axis of the optical fiber. The inclined, reflective surface can be flat, conical or of any other desired shape.

Preferably, the entire metal sheath is made of such a reflective material, providing greater durability than a metal sheath with an insert of a reflective material or a metal sheath plated with one of the aforesaid reflective materials.

When 80 watts of Holmium laser energy (3.07 joules per pulse at 26 hertz) was used through devices with a reflective metal sheath made entirely of very pure silver enclosing a flat ended, low-OH optical fiber positioned opposite a 45° inclined, reflective silver surface in the distal end of a cavity in the metal sheath at its tip, defining a port in the tip for emission of the laser energy, as described above, in in vitro experiments such devices were able in laboratory testing to vaporize soft animal tissue at a higher rate, about 3 grams per minute, than commercially available side firing laser devices employing a beveled optical fiber encased in a capillary tube and enclosed in a polished stainless steel metal sleeve, about 2 grams per minute.

In a further preferred embodiment for the transmission of laser energy at wavelengths of about 1400 to 3000 nanometers, including that of Holmium:YAG laser energy, and wavelengths of about 3000 to 11000 nm nanometers, including CO and $CO_2$ laser energy, using low-OH optical fibers for wavelengths of about 1400 to 2500 nm, ultra low-OH fibers for transmission of wavelengths of about 2500 to 3000 nm or hollow waveguides or fibers of other compositions for transmission of wavelengths of 3000 to 11000 nm, as described above, instead of the distal end of the optical fiber being beveled at an angle of 35° to 40° and enclosed in a closed-ended capillary tube, as described above, the distal end surface of the optical fiber can be flat, positioned opposite an appropriately inclined, highly reflective surface and the distal end portion of the optical fiber can be enclosed in a metal sleeve, as described above, with one difference.

Since wavelengths of light at about 1400 to 3000 nm and higher are highly absorbed by aqueous liquids, such as blood, water or saline used to irrigate the surgical field to provide better visualization, to avoid a portion of the laser energy's being absorbed by such liquids in the space between the distal end face of the optical fiber and the inclined reflective surface, reducing the amount of laser energy emitted toward the target tissue, the distal end portion of the straight ahead-firing optical fiber may be disposed within an open-ended quartz or fused silica capillary tube. Both ends of the capillary tube are fixedly and sealingly affixed within the cavity of the metal sleeve or tip by a heat resistant adhesive, epoxy or gasket material to prevent the ingress of an aqueous liquid, which would be rapidly vaporized into steam and destroy the device.

To more positively fix the open-ended capillary tube within the reflective metal sheath, preferably, each end of the capillary tube fits into a matching recess in the proximal and distal ends of the cavity defined in the metal sheath at its tip, into which recess the adhesive, epoxy or gasket material was earlier deposited. The capillary tube is made of the same type of low-OH or ultra low-OH quartz or fused silica optical fiber used to transmit the aforementioned wavelengths of light. For ease of assembly, the metal sheath should be composed of two components, preferably of the same reflective material with the same coefficient of expansion to avoid loosening of the components at their junction.

In a further preferred embodiment, instead of the open-ended capillary tube described above, a curved or flat window, made of the same material as the optical fiber used to transmit the aforementioned wavelengths of light, may be positioned in the laser energy emission port in the metal sheath and fixedly and sealingly attached therewithin by a heat resistant adhesive, epoxy or gasket material. Preferably, the window is positioned within a matching recess in the wall of the laser energy emission port of the metal sleeve and fixed therein, as described above.

Alternatively, the sheath can be made of surgical grade stainless steel, whose interior and exterior has been plated or coated with a highly reflective material, such as described below, or the interior and exterior of the stainless steel sheath can be encased within one or more tubular metal strips of gold, silver, copper or other reflective material of a suitable thickness, as described heretofore.

The reflective metal strip described above is useful in two additional device embodiments. First, when the distal end of one optical fiber is juxtaposed to the proximal end of another optical fiber, the junction is usually encased in a metal or plastic sleeve. For example, in arthroscopy applications in joints, a short length, for example, about 10 to 25 cm, of an optical fiber is encased in a metal sleeve. The metal sleeve is removably attached to a handpiece fixed over the distal end portion of a 2.5 to 3.0 meter long optical fiber. The short length of optical fiber encased in the metal sleeve is discarded after use, or it can be cleaned, re-sterilized and reused a few times. However, the handpiece and 2.5 to 3.0 meter long optical fiber, which is relatively more expensive, can be cleaned and resterilized and used many times.

Laser energy from imperfections in the optical fiber can be emitted in aberrant directions, causing overheating of the metal or plastic sleeve at the junction point. Also, if the short and long optical fibers are removably joined together or if the optical fibers are not perfectly aligned at the junction point, laser energy will escape, causing rapid overheating of the metal or plastic sleeve at the junction point. Surrounding the area of the junction of two optical fibers with a tubular strip of reflective material, as described above, has been shown in laboratory experiments to reduce or eliminate overheating of the metal or plastic sleeve at the junction point.

In the second device, the proximal end of an optical fiber encased in a metal connector, which is removably attached to the optical coupler of a laser, can be damaged by energy from the laser which misses the core of the optical fiber. Positioning a tubular strip of a reflective material, as described above, between the exterior of the optical fiber, from which the buffer coat and any polymer cladding has been removed, and the interior of the metal connector, can protect the distal end of the optical fiber from erosion and prevent overheating of the metal connector by reflecting stray laser energy back into the optical fiber.

If a hollow quartz or fused silica capillary tube is disposed over the bared distal end of an optical fiber between its exterior and the interior of the metal connector, as described in co-owned U.S. Pat. No. 5,179,610 to Milbum et al., disposing a tubular strip of a reflective material, as described above, between the exterior of the capillary tube and the interior surface of the metal connector can likewise reduce or eliminate erosion of the optical fiber and overheating of the metal connector by reflecting laser energy that misses the core of the optical fiber and enters the capillary tube back into the bared optical fiber. This also protects the laser's optics from back-scattered laser energy from the proximal end of the connector, which is typically made of surgical grade stainless steel.

Referring to FIG. 1, device 20 of the present invention includes a source of laser energy 22, a connector 23, which optically connects optical fiber 24 to laser energy source 22. Optical fiber 24 is about 2 to 5 meters in length, preferably about 3 meters long. Handpiece 25 is fixedly attached to optical fiber 24, terminating about 10 to 60 cm proximally from the distal end of optical fiber 24, preferably about 20 to 40 cm therefrom. If laser energy is emitted at an angle from the axis of optical fiber 24, button 26 on handpiece 25 is disposed on the side of handpiece 25 opposite to the direction of laser energy emission. When the index finger of the surgeon is placed on button 26, the surgeon's index finger points in the direction of laser energy emission.

Figure 2:
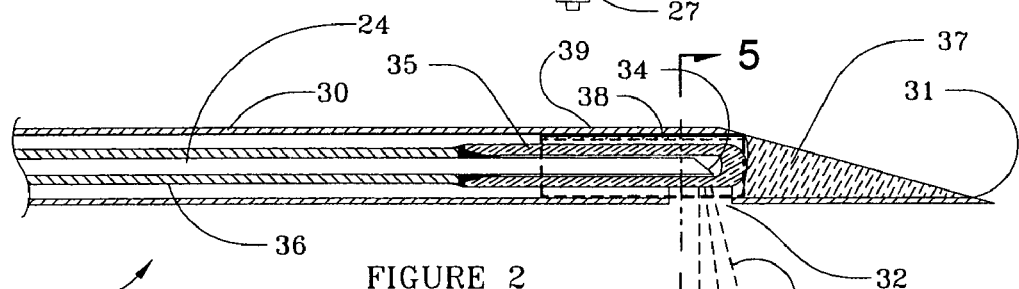
FIG. 2 is a partial, vertical cross-sectional, side view of the distal end portion of the device of the present invention.
Figure 3:
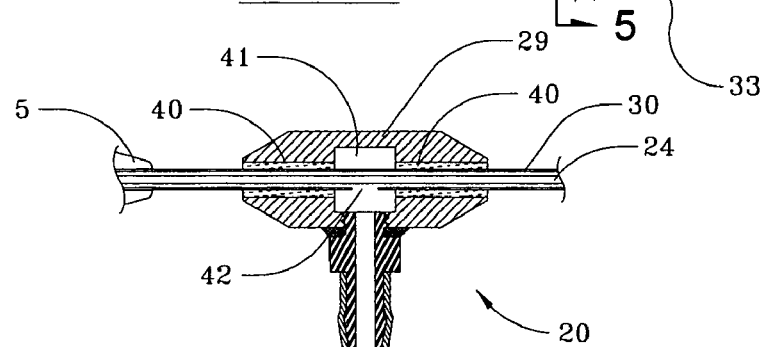
FIG. 3 is a partial, vertical cross-sectional, side view of the fluid infusion or suction channel of the device of the present invention.

Optional luer fitting 27 and attached conduit 28 are in fluid communication with the interior of hollow fitting 29, which is fixedly disposed on a hollow tubular, plastic or metal sheath 30, distally from the distal end of handpiece 25, over an opening 42 in tubular sheath 30 (FIG. 3). The proximal end of sheath 30 is fixedly disposed within the distal end of handpiece 25 by an adhesive or the like. Sheath 30 extends over optical fiber 24 and terminates just beyond the distal end of optical fiber 24, as is illustrated in more detail in FIG. 2. Optional luer fitting 27, conduit 28, and the opening 42 in sheath 30 create a pathway for infusion of a liquid or gas into the space between the exterior of optical fiber 24 and the interior surface of sheath 30. The distal end 31 of sheath 30 may be blunt ended, rounded, pointed or formed into a syringe needle-like shape 31, as shown. Laser energy is emitted from the distal end of optical fiber 24 by the means described in FIG. 2 below exits emission port 32 in sheath 30 as shown by arrows 33. Sheath 30 may be made of a heat resistant plastic or a metal, preferably medical grade stainless steel, and the like.

As illustrated in FIG. 2, the distal end of optical fiber 24 has been beveled at an angle of about 30° to 50° from the axis of the optical fiber 24, preferably at an angle of about 35° to 40° therefrom, most preferably at about 39°, forming reflective surface 34. Capillary tube 35, whose distal end has been closed by thermal fusing, encases the distal end portion of optical fiber 24. The proximal end of capillary tube 35 may be attached by an adhesive or the like to the glass cladding of optical fiber 24, from whose distal end portion any polymer cladding and the buffer coat has been a removed. The distal end of closed-ended capillary tube is attached to the glass cladding of optical fiber 24, or to optical fiber 24 itself, by thermal fusing.

Capillary tube 35 creates an air environment at beveled, reflective surface 34 of optical fiber 24, and light energy emitted into the proximal end of optical fiber 24 is almost entirely directed, by total internal reflection, from beveled, reflective surface 34 of optical fiber 24 at an angle of about 75° to 85° (if the bevel is at 39°) from the axis of optical fiber 24 and exits sheath 30 through laser energy emission port 32, as shown by arrows 33.

If the distal end of sheath 30 is formed into a needle-like shape, as shown, the distal end of sheath 30 may be closed by metal or adhesive plug 37. Reflective metal strip 38 is disposed between and occupies all or most of the space between the inner surface of sheath 30 and the non-energy emitting surface 39 of capillary 35. Reflective metal strip 38 does not extend over the energy emitting surface of capillary tube 35, however, so that laser energy can be emitted through emission port 32 in sheath 30, as indicated by arrows 33.

As seen in FIG. 3, the proximal and distal ends of optional hollow fitting 29 of device 20 are attached by adhesive 40 to the exterior of sheath 30. Luer fitting 27 and conduit 28 are in fluid communication with cavity 41 in fitting 29 and opening 42 in tubular sheath 30, which enables a liquid or gas to be infused into or a vacuum to be drawn through the space between optical fiber 24 and the interior surface of sheath 30. Alternatively, adhesive 40 may be replaced by a gasket material which enables fitting 29 to rotate about sheath 30, but which prevents leakage of fluid from fitting 29.

Figure 4:
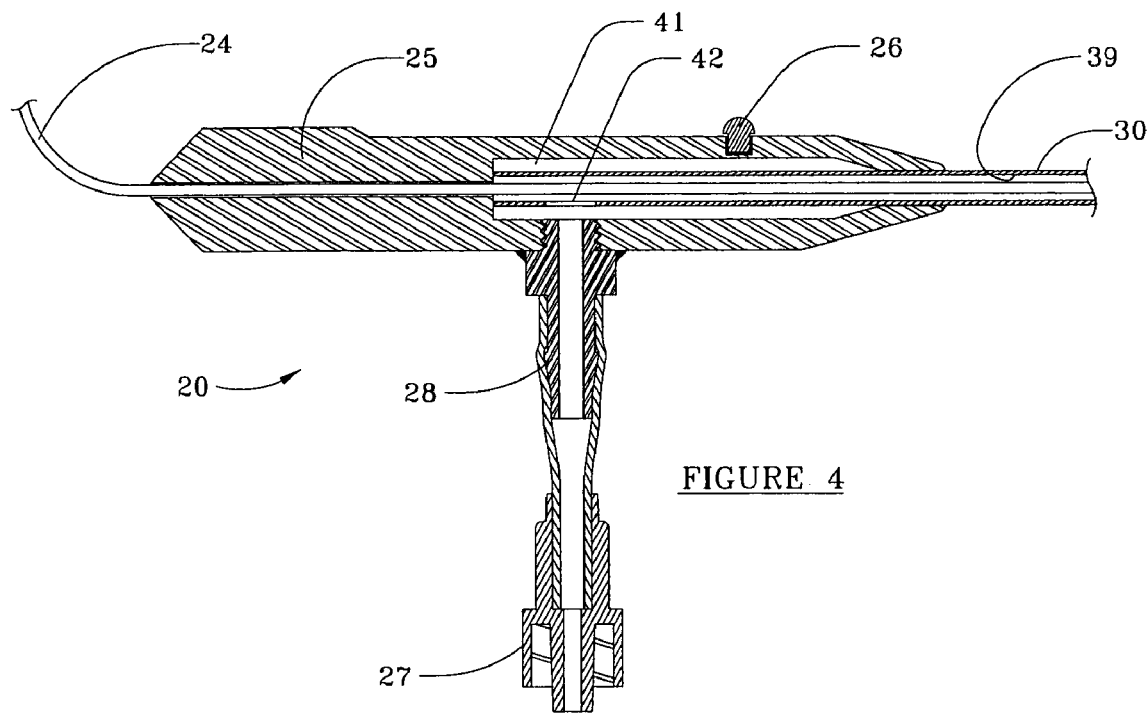
FIG. 4 is a partial, vertical cross-sectional, side view of an alternative infusion or suction channel of the device of the present invention.

Alternatively, as seen in FIG. 4, optional luer fitting 27 and conduit 28 are in fluid communication with cavity 41 in handpiece 25. Opening 42 in tubular sheath 30, enables a gas or liquid to be infused into or a vacuum to be drawn through the space between optical fiber 24 and the interior surface 39 of sheath 30.

Figure 5:
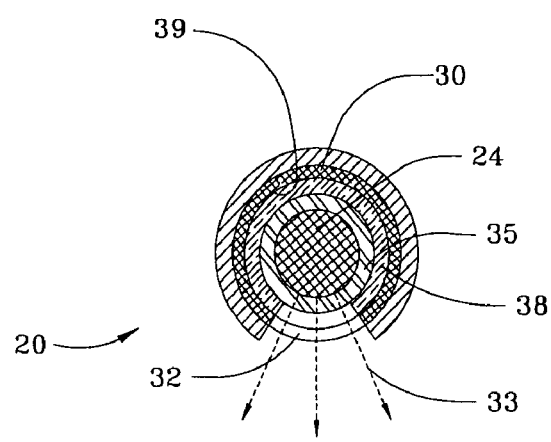
FIG. 5 is a vertical cross-sectional view of the distal end portion of the device of the present invention taken at plane 5-5 in FIG. 2.

FIG. 5 is a cross-sectional view of the distal end of device 20 taken along plane 5-5 of FIG. 2. Reflective metal strip 38 is preferably positioned in abutting relationship against the inner surface 39 of sheath 30 and surrounds capillary tube 35, except for energy emission port 32, and almost completely fills the space between the outer surface of capillary tube 35 and the inner surface 39 of sheath 30, over preferably about 200° to 330° thereof, most preferably about 240° to 300° thereof. When a liquid or gas is infused into the space between the exterior of capillary tube 35 and the inner surface 39 of sheath 30, reflective metal strip 38 obstructs fluid flow except over the energy emitting portion of capillary tube 35 and emission port 32 of tubular sheath 30. This forces a larger volume of fluid to flow over the energy emitting surface of capillary tube 35 and the inner surface 39 of sheath 30 containing emission port 32, cooling and flushing debris from both.

Metal strip 38 reflects some of the stray energy emissions, due to the curvature of capillary tube 35 or from imperfections in beveled surface 34 and capillary tube 35, out through the emission port 32. Reflective metal strip 38 also reflects some of the laser energy back-scattered from the target tissue through port 32 and away from the back of non-energy emitting surface 39 of sheath 30, avoiding overheating of sheath 30.

The emission of laser energy from beveled, reflective surface 34 (FIG. 2) of optical fiber 24 through emission port 32 of sheath 30 in the desired direction is shown by arrows 33. While not separately shown in FIGS. 2 or 5, optionally, a washer-shaped ring of reflective metal may be affixed by an adhesive or other bonding method to proximal end face of capillary tube 35 to prevent damage or overheating of sheath 30 from laser energy back-scattered from the target tissue being transmitted backward through capillary tube 35.

Figure 6:
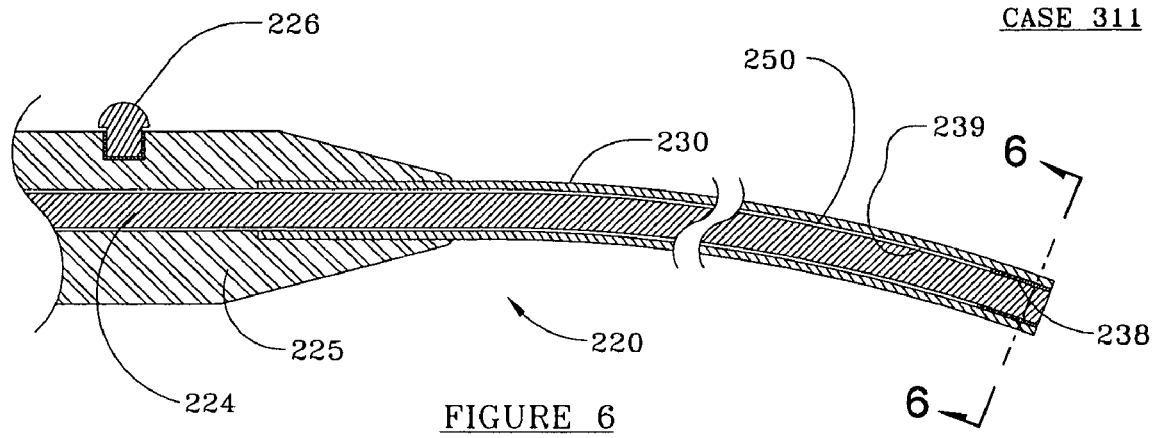
FIG. 6 is a partial, vertical cross-sectional, side view of the distal end portion of the device of the present invention.

FIG. 6 illustrates a device embodiment 220, wherein optical fiber 224 extends through handpiece 225 and attached metal sheath 230, whose distal end portion is bent at an angle of about 20°, such as for use in arthroscopy. For other applications, the distal end of sheath 230 may be straight or bent at any desired angle up to about 60°. Sheath 230 can also be formed of a rigid, heat resistant plastic, such as Teflon® or PEEK®. Button 226 is disposed on the side of handpiece 225 opposite the direction in which the distal end of sheath 230 is bent.

Figure 7:
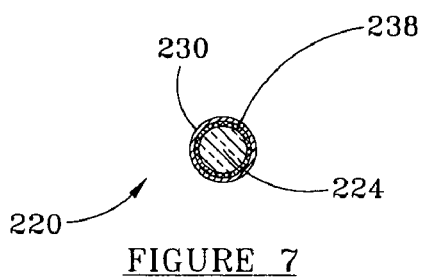
FIG. 7 is a cross-sectional view taken at plane 6-6 of FIG. 6.

FIG. 7 illustrates the disposition of reflective metal strip 238 in device 220 of FIG. 6 between the exterior of the distal end portion of optical fiber 224 and the interior of the distal end portion of metal or plastic sheath 230.

Reflective metal strip 238 provides a reflective surface and is disposed within the distal 1 to 3 cm of sheath 230, is attached to the interior surface of the sheath 230 by an adhesive or the like and occupies substantially all of the space between the exterior surface of optical fiber 224 and the interior surface 239 of the sheath 230. The disposition of reflective metal strip 238 between the outer surface of the fiber 224 and the inner surface 239 of sheath 230 in the distal 1 to 3 cm of sheath 230 creates and defines an elongate hollow space 250 between the fiber 224 and sheath 230 in the region of sheath 230 located aft of strip 238, which can be filled with an adhesive or the like, if desired.

Figure 8:
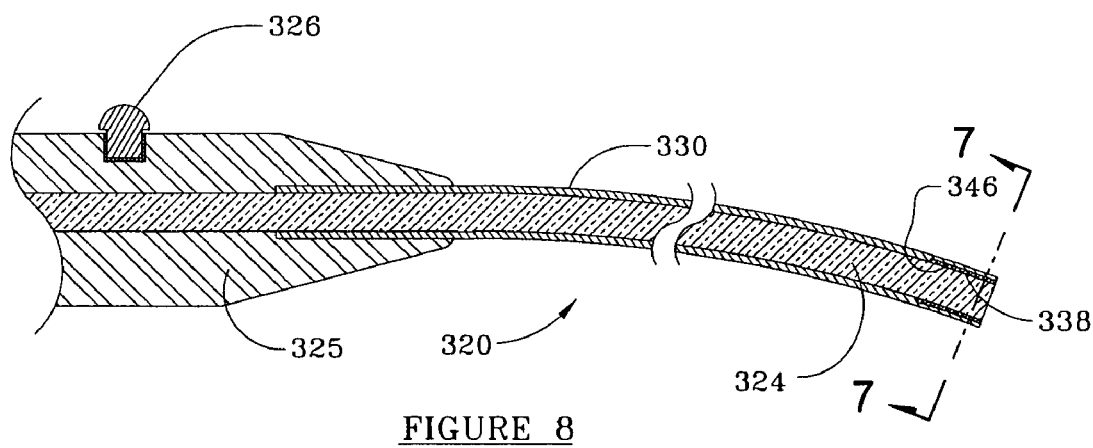
FIG. 8 is a partial, vertical cross-sectional, side view of an alternate embodiment of the device of FIG. 6.

FIG. 8 illustrates yet another embodiment of device 320 of the present invention, wherein about 1 to 3 cm of the interior surface of the hollow distal end portion of metal or plastic sheath 330 has been drilled out and defines an elongate circumferential recess 346 or depression adapted to accept the reflective metal strip 338, which has been formed into a tubular shape and fixed within recess 346 by an adhesive or the like. The thickness of the wall of sheath 330 that has been recessed and removed, in this embodiment, is equal to the thickness of reflective metal strip 338, forming a smooth, contiguous inner surface for insertion of optical fiber 324 thereinto. Sheath 330 can be formed of metal, or of a rigid, heat resistant plastic, such as Teflon® of PEEK®. Button 326 is disposed on the side of handpiece 325 opposite the direction in which the distal end of sheath 330 is bent.

Figure 9:
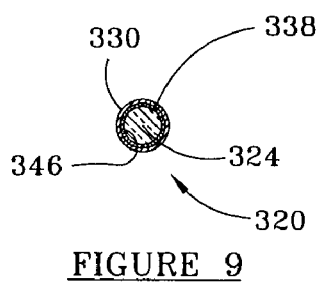
FIG. 9 is a cross-sectional view taken at plane 7-7 of FIG. 8.

FIG. 9 illustrates the disposition of reflective metal strip 338 in device 320 of FIG. 8 between the exterior of optical fiber 324 and the interior of drilled out recess 346 defined in the interior surface of the distal end portion of metal or plastic sheath 330. The advantage of the embodiment shown in FIGS. 9 and 10 is that it permits the outside diameter of sheath 330 to be reduced by the thickness of the reflective metal strip 338, enabling it to be inserted into tissue with less trauma and to access tissues which may otherwise be difficult or impossible to reach. In the embodiment of FIGS. 8 and 9, the outer surface of optical fiber 324 abuts against the inner surface of the sheath 330 along a substantial portion of the length of the sheath 330 and against the inner surface of the reflective metal strip 338 along the remaining 1 to 3 cm of the length and distal end portion of the sheath 330.

FIG. 10 illustrates a further device embodiment 420, wherein a first reflective metal strip 450 extends around the outer surface of optical fiber 424, between optical fiber 424 and interior surface 439 of sheath 430, and a second reflective metal strip 452 extends around the outer surface of the distal 1 to 3 cm of sheath 430. Additionally, a third strip of reflective material 454, or an extension of metal strip 450 or 452, extends around and covers the distal, radial end face of the sheath 430. Strips 450, 452 and 454 can be unitary with each other so as to define an end reflective metal cap 458 adapted to be fitted over the radial end face of sheath 430.

Sheath 430 can be formed of metal, or of a rigid, heat resistant plastic, such as Teflon® or PEEK®. Button 426 is disposed on the side of handpiece 425 opposite the direction in which the distal end of sheath 430 is bent. While this embodiment is less expensive to manufacture, it creates a device having diameter at the distal end of sheath 430 which is larger than the devices of FIGS. 7 or 9. While not separately shown in FIG. 11, recesses on the exterior and interior of the distal end of sheath 430 may be created to depths equal to the thicknesses of metal strips 450 and 452, providing a smaller outside diameter and contiguous inner and outer surfaces as described in FIGS. 6 and 8.

An optical fiber encased in a connector, removably attached and optically coupled to a laser, a short length of optical fiber encased in a metal sheath used in arthroscopy procedures, which entails the junction of one optical fiber removably juxtaposed to another optical fiber within a handpiece/long optical fiber assembly, and an optical fiber whose distal end is positioned opposite a reflective metal surface can be eroded during use from laser energy that misses the core of the optical fiber or is back-scattered from the target tissue or from imperfections in the optical fiber.

FIG. 11 illustrates device embodiment 520, in which optical fiber 524(a) extends from a source of laser energy (not separately shown). Optical fiber 524(a) has a quartz or fused silica core, surrounded by a glass cladding (not separately shown), and, typically, a polymer cladding and buffer coating 537. Optical fiber 524(a) is encased in plastic or metal sheath 530. Polymer cladding and buffer coating 537 have been removed from the distal end portion of optical fiber 524(a), which protrudes distally from the distal end of metal sheath 530. The exposed, bare, distal end of optical fiber 524(a) functions as a male member for insertion into female cavity 552 of device 521, as shown in FIG. 12.

FIG. 12 illustrates device embodiment 521 having a proximal, female cavity 552, which mates with the male, bared, distal end of optical fiber 524(a) of device 520 shown in FIG. 11. Optical fiber 524(b) typically has a quartz or fused silica core, surrounded by a glass cladding (not separately shown) and, typically, a polymer cladding and buffer coating 537. Optical fiber 524(b) is encased hollow plastic or metal sheath 530, which extends over optical fiber 524(b) and extends proximally from the proximal end of optical fiber 524(b). Polymer cladding and buffer coating 537 have been removed from the proximal end portion of optical fiber 524(b).

Hollow quartz or fused silica capillary tube or sleeve 541 is attached by an adhesive or epoxy to the interior of the sheath 530, extends over the bared distal end portion of optical fiber 524(b), extends proximally from the distal end of optical fiber 524(b) and co-terminates with the proximal end of hollow metal or plastic sheath 530, defining a female channel or cavity 552 in the proximal end of sheath 530, to receive bared, optical fiber 524(a) of device 520 of FIG. 11.

Reflective metal strip 538 is formed into a tubular shape and attached within the interior of the proximal end of hollow metal or plastic sheath 530 by an adhesive or the like, filling the space between the exterior of capillary tube or sleeve 541 and the interior of sheath 530. Metal strip 538 extends over the exterior of capillary tube 541 and covers the distal end of capillary tube 541. The proximal end face of capillary tube 541, into which bared optical fiber 524(a) is to be inserted, has a beveled inner surface 539, which guides bared optical fiber 524(a) into its hollow interior. Optionally, if desired, metal trip 538 can also extend over the proximal end of capillary tube 541, as shown.

The length of cavity 552 of FIG. 12 and the length of the bared distal end portion of optical fiber 524(a) of FIG. 11 are such that a space of about 10 to 70 thousandths of an inch is left between the distal end of optical fiber 524(a) and the proximal end of optical fiber 524(b), so that neither is damaged when brought close together.

Metal sheath 530, after insertion into a handpiece (not separately shown), can be removably fixed within the handpiece by a threaded or locking mechanism (not separately shown), as known in the art.

In conventional junctions of optical fibers, some laser energy will be reflected from the proximal end of optical fiber 524(b) or may miss the distal end of optical fiber 524(b), causing handpiece 525 (not separately shown) to overheat at the junction of the optical fibers, which could damage the device or injure the holder.

Some of the light energy reflected from the proximal end of optical fiber 524(b) passes through quartz or fused silica sleeve 541 and is reflected by metal strip 538, back through quartz or fused silica capillary tube 541 into the bared portions of optical fibers 524(a) and 524(b). Also, some of the light energy that misses the distal end of optical fiber 524(b) passes through quartz or fused silica capillary tube 541 and is reflected by metal strip 538, back through quartz or fused silica capillary tube 541 into the bared portion of optical fibers 524(a) and 524(b).

Such devices can also be constructed without a quartz or fused silica capillary tube 541. In such devices, quartz or fused silica capillary tube 541 is replaced by a metal sleeve 541, for example, made of surgical grade stainless steel. Tubular reflective metal strip 538 is attached within the interior of metal sleeve 541 with an adhesive or epoxy or may be similarly attached within a recess of equal depth in the inner wall of metal sleeve 541, as described above, creating a smooth, contiguous interior.

Alternatively, metal sleeve 541 may be electroplated with copper, silver or gold, preferably silver, with a thickness of at least about 3 to 10 thousandths, preferably about 5 to 6 thousandths. Most preferably, for greater durability, metal sleeve 541 can be made entirely of a reflective material, such as gold, silver, copper or a dielectric, preferably silver, for the reasons cited above, or can be plated to provide a reflective surface.

The benefit of this embodiment of the present invention is it avoids overheating of handpiece 525 at the junction of optical fibers 524(a) and 524(b), which could damage the device or injure the operator, as well as requiring the device to be discarded, increasing the cost of the procedure. It also enables metal sheath 530, containing a short length of optical fiber 524(b), for example, about 10 to 40 cm in length, to be discarded after one or a few uses, while handpiece 525 and the long 2.5 to 3 meter length of optical fiber 524(a), which is relatively expensive, may be cleaned, sterilized and re-used many times, reducing the cost of the procedures in which it is used.

Figure 13:
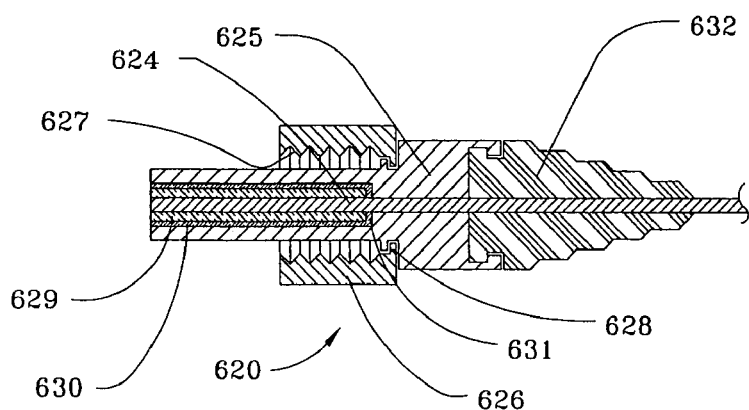
FIG. 13 is a partial, vertical cross-sectional view of the proximal end portion of a device of the present invention.

FIG. 13 illustrates the principles of the present invention applied to connector 620, which encases the proximal end of optical fiber 624 and enables optical fiber 624 to be optically coupled to the source of laser energy. As shown, metal connector 620 has two components, base 625 and nut 626 with threaded extension 627. Nut 626 rotates around base 625 about retaining ridge 628 thereof. Threads 627 of nut 626 engage threads (not shown) of the optical coupler of the source of laser energy, and enable connector 620 and optical fiber 624 to be removably attached to and optically coupled to said source of laser energy.

The buffer coat and any polymer cladding have been removed from the proximal end portion of optical fiber 624, and the so exposed end portion is situated within the base 625 and is surrounded by a transparent quartz or fused silica sleeve 629 illustrated in co-owned U.S. Pat. No,. 5,179,610 to Milburn et. al. Sleeve 629 is, in turn, surrounded by a reflective material 630, such as a tubular piece of reflective metal, as described heretofore. Material 630 also extends over the end portion 631 of transparent sleeve 629 and prevents any aberrant emissions of laser energy from said source of laser energy and any emissions of laser energy from said source that miss the core of optical fiber from being transmitted through sleeve 629 to body 625 of connector 620 and causing it to overheat, melting and failure of optical fiber 624 and possibly injuring the surgeon. Rubber or plastic strain relief 632 extends from within body 625 of connector 620 distally about 2 to 10 cm over optical fiber 624.

Connector 620 can also be made, as described above, but without sleeve 629, in which event, tubular reflective material 630 is disposed between the exterior of glass cladding (not separately shown) of optical fiber 624 and the interior of body 625 of connector 620.

Figure 14:
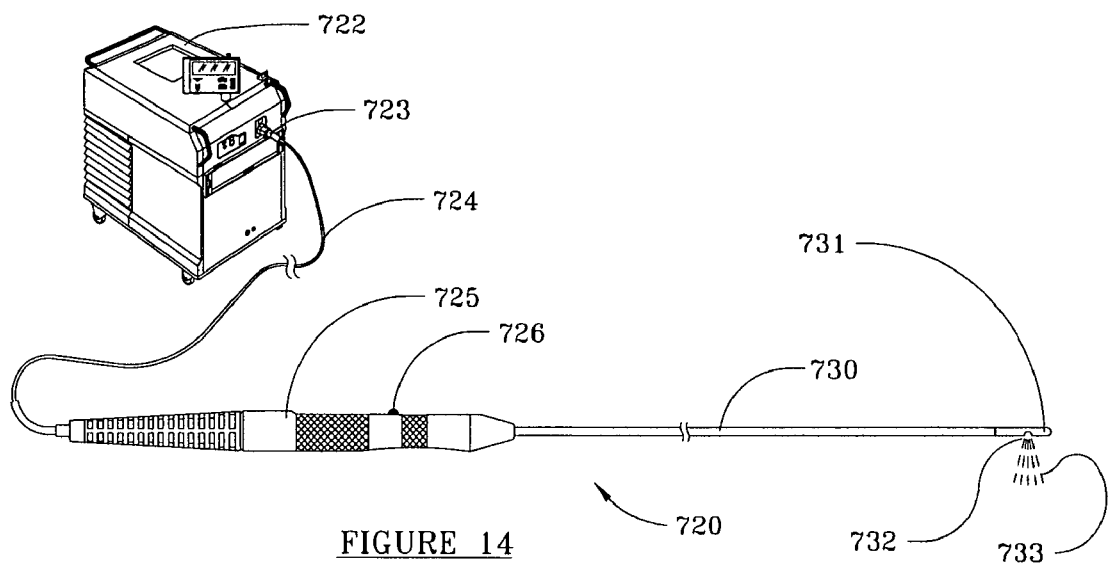
FIG. 14 is a vertical, exterior view of a preferred embodiment of the device of the present invention.

FIG. 14 illustrates a preferred embodiment of the present invention for laterally delivering laser energy at wavelengths of 300 to 1400 nm. Device 720 includes a source of laser energy 722 of 300 to 1400 nm and connector 723, which encases the bared proximal end portion of optical fiber 724. Optical fiber 724 extends through handpiece 725, with button 726 mounted on handpiece 725 on the side opposite that of the direction of emission of laser energy.

Figure 15:
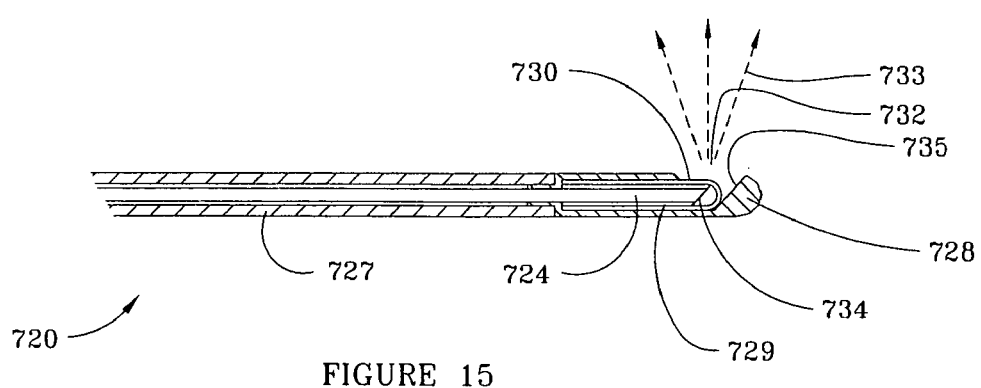
FIG. 15 is a partial, vertical cross-sectional view of the distal end portion of the device of the present invention shown in FIG. 14.
Figure 16A:
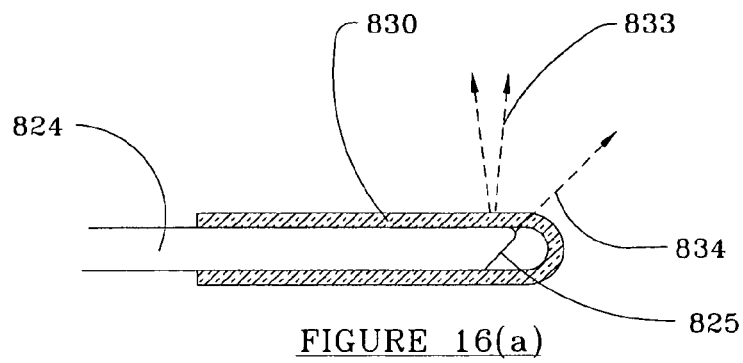
FIG. 16(a) is a partial, vertical, cross-sectional view of a conventional optical fiber device after use.
Figure 16B:
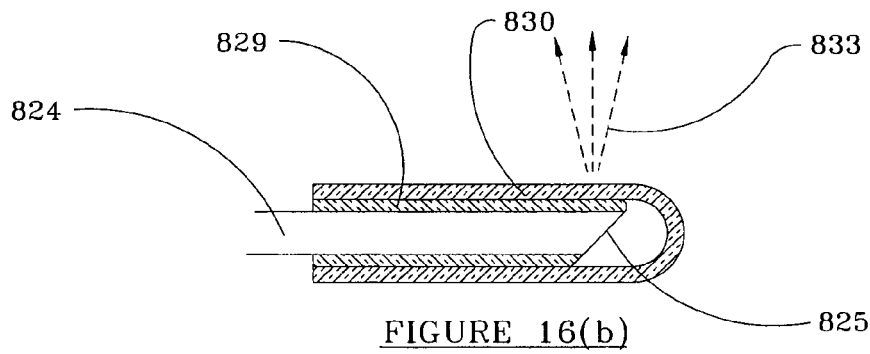
FIG. 16(b) is a partial, vertical cross-sectional view of a preferred embodiment of the optical fiber device of FIG. 16(a) after use.
Figure 16C:
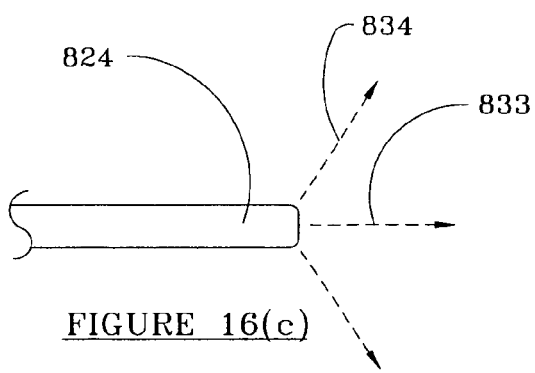
FIG. 16(c) is a partial, vertical cross-sectional view of a conventional side firing, optical fiber device after use.
Figure 16D:
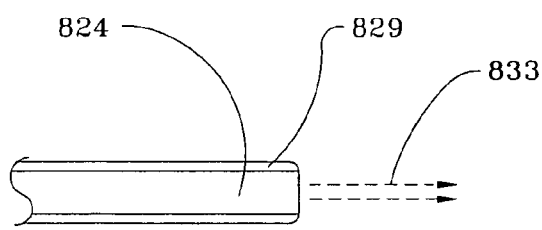
FIG. 16(d) is a partial, vertical cross-sectional view of a preferred embodiment of the side-firing optical fiber device of FIG. 16(c) after use.

Plastic or metal sheath 727 (FIG. 15) extends distally from within handpiece 725 and terminates in reflective metal endpiece 728, which is made entirely of gold, silver, copper or other reflective material, preferably silver, as described heretofore.

The buffer coat and any polymer cladding have been removed from the distal end portion of optical fiber 724. In this embodiment, a quartz or fused silica transparent capillary tube 729 has been fused to the bared distal end portion of optical fiber 724, and the proximal end portion of open ended capillary tube 729 may be attached by a heat resistant epoxy or adhesive to optical fiber 724. The distal end of the combined optical fiber 724/capillary tube 729 have been beveled at an angle of about 35° to 40° from the axis of optical fiber 724, preferably about 39°, after which the beveled surface 734 of the assembly is polished.

A second capillary tube 730, whose distal end has been closed by thermal fusion, is disposed over the beveled optical fiber 724/capillary tube 729 assembly. The distal end portion of capillary tube 730 is fused to the beveled optical fiber 724/capillary tube 729 assembly at the area of laser energy transmission. The proximal end of closed-ended capillary tube 730 is preferably attached to the optical fiber 724/capillary tube 729 assembly by a heat resistant adhesive or epoxy.

Reflective metal endpiece 728 of sheath 727 provides a reflective surface and is attached to the portion of optical fiber 724 distal, merges with plastic or metal sheath 727 and extends over the beveled optical fiber 724/capillary tube 729 assembly and capillary tube 730, as shown. Since capillary tube 730 creates an air interface opposite the about 35° to 45°, preferably 39°, beveled surface of the capillary tube 729 and optical fiber 724 assembly, laser energy is emitted from emission port 732 at about 75° to 90° from the axis of optical fiber 724 as indicated by arrows 733. A cavity in reflective metal endpiece 728 defines both laser energy emission port 732 and the compartment in which capillary tube 730 and the capillary tube 729/optical fiber 724 assembly are disposed.

The distal end of the cavity in metal endpiece 728 can be rounded, but is preferably flat and inclined at an angle of about 45° from the axis of optical fiber 724, as shown, defining reflective surface 735. In the event capillary tube 730 is damaged or fractures, laser energy will be reflected laterally by reflective surface 735.

If capillary tube 730 has about the same thickness as capillary tube 35 of FIG. 2, the overall diameter of the assembly of optical fiber 724/capillary tube 729 and closed-ended capillary tube 730 and metal tip 731 are larger than the overall diameter of the device of FIGS. 1 and 2, due to the addition of capillary tube 729. This may necessitate the use of an endoscope with a larger instrument channel.

To maintain the same outside diameter of device 720 as that of device 20, with the same thickness of capillary tube 730 as capillary tube 35 of FIG. 2, if desired, instead of an optical fiber with a 550 micron core diameter, an optical fiber with a core diameter of 365 to 450 microns may be used, preferably about 400 microns, enabling the diameter of the assembly to be comparable to that of the device of FIGS. 1 and 2.

The benefit of fusing the distal end of capillary tube 729 to the glass cladding (not separately shown) of optical fiber 724, as described above in FIG. 15, is illustrated in FIGS. 16(*a*) and 16(*b*).

In FIG. 16(*a*), an optical fiber 824, whose distal end surface 825 has been beveled at an angle of about 30° to 50°, preferably about 39°, is encased within capillary tube 830. As a result of laser energy back-scattered from the target tissue and reflected from the curved inner surface of outer, closed-ended capillary tube 830 erodes the thin, leading edge of beveled surface 825 of optical fiber 824, causing some of the laser energy to be totally internally reflected in the desired direction, as shown by arrows 833, and some to be emitted from the eroded leading edge of beveled surface 825 at an undesired angle, as shown by arrows 834.

In FIG. 16(*b*), capillary tube 829 is fused to the distal end portion of optical fiber 824 and situated within outer capillary tube 830. Capillary tubes 829 and 830 are concentric relative to one another. Due to the fusing of the distal end of capillary tube 829 to optical fiber 824 and the distal end of the capillary tube 829/optical fiber 824 assembly being beveled and polished as described above, the thin, leading edge of beveled surface 825 of capillary tube 829 is likewise eroded in use, but the erosion does not affect the total internal reflection of laser energy in the desired direction or diminished its fluence, as shown by arrows 833, as optical fiber 824 of the capillary tube 829/optical fiber 824 assembly has not been eroded.

As seen in FIG. 16(*c*), when the distal edges of optical fiber 824 are eroded, most of the laser energy is emitted straight ahead, as shown by arrow 833, some of the laser energy is emitted in aberrant directions, as shown by arrows 834.

As shown in FIG. 16(*d*), when the distal end portion of optical fiber 824 is encased, wholly or partially by thermal fusion, in quartz or fused silica capillary tube 829, which preferably has the same OH content as optical fiber 824 and the distal edges of capillary tube 829 are eroded during use. The laser energy is emitted forwardly without diminution, as shown by arrows 833, when optical fiber 824 of the optical fiber 824/capillary tube 829 assembly is not eroded.

Figure 17:
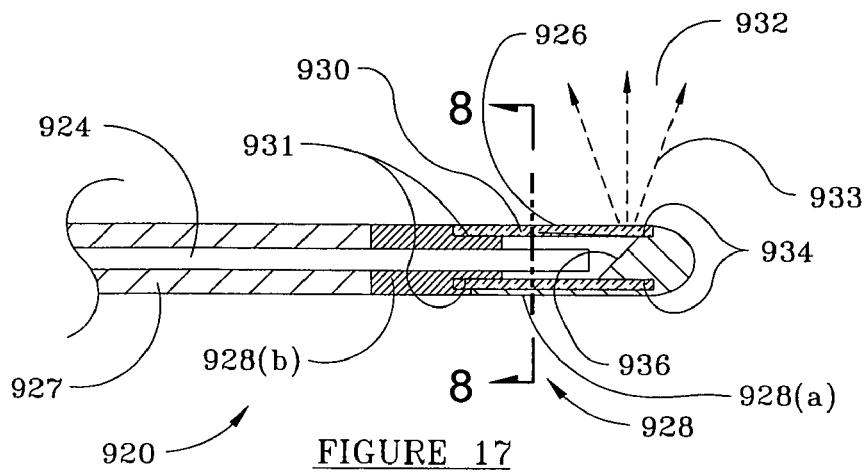
FIG. 17 is a partial, vertical, cross-sectional view of the distal end portion of a preferred embodiment of the present invention.

FIG. 17 illustrates a preferred embodiment of the present invention for use with laser energy of wavelengths of about 1400 to 3000 nm. As shown, device 920 includes reflective metal endpiece 928 of sheath 927. Endpiece 972 is made of two components, distal portion 928(*a*) and proximal portion 928(b), both of which are made of the same reflective material, preferably silver, as described heretofore, to avoid loosening their attachment to each other due to different coefficients of expansion when heated.

In assembly, optical fiber 924 is attached by an adhesive or epoxy within plastic or metal sheath 927, and proximal metal endpiece portion 928(b) is attached to sheath 927 by pressure fitting, crimping, an adhesive or matching threads, or a combination of two or more of such means, as known in the art. The proximal end of hollow capillary tube 930, which is substantially cylindrical and made of low-OH quartz or fused silica for transmission of the said wavelengths, is positioned in recess 931 of proximal endpiece portion 928(b), earlier filled with a high temperature adhesive or epoxy to sealingly affix the proximal end of capillary tube 930 therewithin, with laser energy emitting surface 926 of capillary tube 930 being flush with the exterior of proximal metal tip 928(b).

The distal end of capillary tube 930 is likewise positioned in recess 934 in distal endpiece portion 928(a) and fixedly and sealingly held therein by a high temperature adhesive or epoxy. Distal endpiece portion 928(a) may be fixedly and sealingly attached to proximal endpiece portion 928(b) by pressure fitting, matching threads, crimping or an adhesive or epoxy, or a combination of two or more of such means, as known in the art.

Proximal endpiece portion 928(a) has a reflective surface 936 inclined at an angle of about 35° to 50°, preferably about 45° for reflection of the laser energy at an angle of about 90° from the axis of optical fiber 924, out of emission port 932 as shown by arrows 933. Capillary tube 930 prevents aqueous liquids from entering the space between the distal end of optical fiber 924 and inclined reflective surface 936 of distal endpiece portion 928(a), which would consume a portion of the laser energy and create an undesirable steam bubble.

Figure 18:
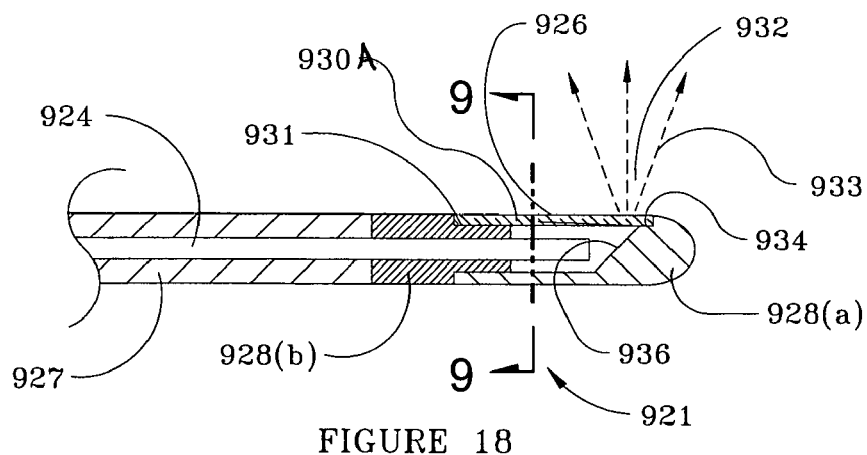
FIG. 18 is a partial, vertical, cross-sectional view of an alternative preferred embodiment of the present invention.

In FIG. 18, a window is defined by a hollow capillary tube portion 930A of low-OH quartz or fused silica, whose distal and proximal ends are disposed within recesses 934 and 931 in the walls of distal and proximal endpiece portions 928(a) and 928(b), respectively, and are fixedly and sealingly attached therein by a high temperature adhesive, epoxy or gasket material. Instead of a capillary tube, a curved (as shown) or flat window 930 can be provided in device 921 to prevent the ingress of liquid for the reasons cited above.

A hollow tube is preferred over a flat window, however, as its side walls enable it to be more safely constrained within recesses 934 and 931 in endpiece portions 928(a) and 928(b), and its energy emitting window 926 is flush with the exterior of metal endpiece portions 928(a) and (b), with less fluid intervening between sheath endpiece 928 and the target tissue to absorb and diminish the amount of laser energy reaching the target tissue. Curved window defined by tube portion 930A can extend over about 60° to 200° of the exterior surface of metal endpiece 928, preferably over about 90° to 180° of the surface thereof.

Other means can be used to safely fix and seal capillary tube 930 of FIG. 17 or window or tube portion 930A of FIG. 18 in metal endpiece 928, as known in the art.

Figure 19A:
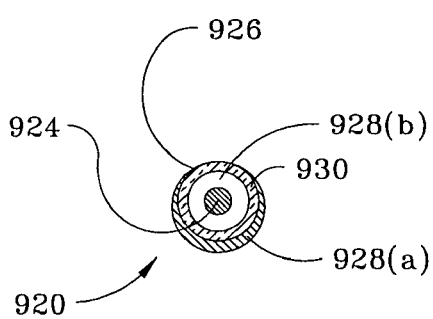
FIG. 19(a) is a cross sectional view at plane 8-8 of the device of FIG. 17.

As shown in FIG. 19(a), the distal end portion of device 920 of FIG. 17 includes distal metal endpiece portion 928(a), in which eccentric recess 934 is provided to accept the distal end of capillary tube 930, whose outside diameter is smaller than the outside diameter of metal endpiece portion 928(a). In this particular embodiment, the energy emitting window defined by surface 926 of capillary tube 930 is flush with the exterior of metal endpiece portion 928(a). The sides and bottom portions of capillary tube 930 are held in place in recess 934 in distal metal endpiece portion 928(a) and may be fixedly and sealingly attached therein with an adhesive, epoxy or gasket material, as known in the art. The same construction applies to proximal metal endpiece portion 928(b), in which the proximal end of capillary tube 930 fits into a portion of eccentric recess 931 and is fixedly and sealingly attached therein as described above.

Figure 19B:
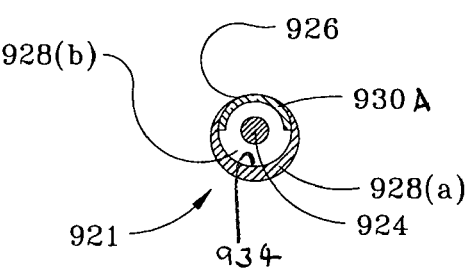
FIG. 19(b) is a cross sectional view at plane 9-9 of the device of FIG. 18.

As shown in FIG. 19(b), device 921 of FIG. 18 includes proximal metal endpiece portion 928(a), in which recess 934 has been provided as described above to accept the proximal end of tube portion 930A, whose outside diameter (O.D.) is smaller than the O.D, of proximal metal endpiece portion 928 (a). As shown, tube portion 930A is half or 180° of a cylinder, and the sides of tube portion 930A are mechanically constrained in recess 934 of metal endpiece portion 928(a). The proximal end of tube portion 930A may be fixedly and sealingly attached as described above. Tube portion 930A can be as small as about one-fourth of a circle, or 90°, and still be mechanically constrained in recess 934 of metal sleeve 928 (a).

The construction of metal endpiece portion 928(b) is the same as that of endpiece portion 928(a), in which the distal end of partially circular capillary tube 930 fits into eccentric recess 931 of metal endpiece 928(b) and is fixedly and sealingly attached therein as described above.

When the devices of FIGS. 17 or 18 are used in contact or near contact with tissue, there is little aqueous fluid between top surface 926 of capillary tube 930 and the target tissue. When laser energy at wavelengths of about 1400 to 3000 nm, including Holmium laser energy, is transmitted through optical fiber 924 and reflected laterally from inclined reflective surface 936 of distal metal endpiece portion 928(a), little energy is wasted in vaporizing the intervening liquid.

For transmission of wavelengths of laser energy at 300 to 1400 nm, a single or dual component metal sheath endpiece 928, such as shown in FIGS. 17 and 18 can be used but without circular capillary tube 930 or FIG. 17 or partially circular capillary tube 930 of FIG. 18, as such wavelengths are not highly absorbed by aqueous liquids such as water, saline or blood and pass through the intervening liquid without substantial energy loss.

The foregoing description and drawings are intended as illustrative, and are not to be taken as limiting. Still other variations within the spirit and scope of the present invention are possible and will really present themselves to those skilled in the art.

We claim:

1. A laser device comprising:
   a source of laser energy;
   a laser energy conduit adapted for connection to the laser energy source and including a proximal end portion for coupling to the laser energy source and a distal end portion from which laser energy can be emitted;
   a sheath surrounding at least part of the distal end portion of said laser energy conduit and defining a window through which laser energy emitted from the distal end portion of said laser energy conduit can pass; and
   a reflective surface at the distal end portion of said laser energy conduit situated between the laser energy conduit and the sheath for reflecting away from the sheath stray laser energy emitted from said laser energy conduit.

2. The laser device of claim 1 wherein the reflective surface is defined by a material located at the distal end portion of said laser energy conduit and situated for reflecting stray laser energy emitted from said laser energy conduit through said window in said sheath.

3. The laser device of claim 1 wherein the sheath includes an inner surface and terminates in an endpiece, a portion of which defines a cavity, and wherein a portion the reflective surface is located in said cavity.

4. The laser device of claim 1 wherein the reflective surface is defined by the sheath, the device further comprises a transparent tubular sleeve, and the sleeve surrounds the distal end portion of said laser energy conduit.

5. The laser device of claim 4 wherein the sheath is made of gold, silver or copper, and the sleeve is transparent.

6. The laser device of claim 5 wherein the sleeve is made of quartz or fused silica.

7. The laser device of claim 4 wherein the sheath is made of silver and is concentric with the sleeve.

8. A laser device comprising:
a source of laser energy;
a laser energy conduit adapted for connection to the laser energy source and including a proximal end portion for coupling to the laser energy source and a distal end portion from which laser energy can be emitted;
a sheath surrounding at least part of the distal end portion of said laser energy conduit and defining a window through which laser energy emitted from the distal end portion of said laser energy conduit can pass; and
a reflective surface at the distal end portion of said laser energy conduit situated between the laser energy conduit and the sheath for reflecting away from the sheath stray laser energy emitted from said laser energy conduit;
wherein the reflective surface is defined by a material located at the distal end portion of said laser energy conduit and situated for reflecting stray laser energy emitted from said laser energy conduit through said window in said sheath and
wherein a capillary tube envelops the distal end portion of said laser energy conduit and said reflective surface surrounds a major portion but not all of said capillary tube.

9. The laser device of claim 8 wherein the sheath has an inner surface and said reflective surface is defined by a material abutted against the inner surface of said sheath.

10. A laser device comprising:
a source of laser energy;
a laser energy conduit adapted for connection to the laser energy source and including a proximal end portion for coupling to the laser energy source and a distal end portion from which laser energy can be emitted;
a sheath surrounding at least part of the distal end portion of said laser energy conduit and defining a window through which laser energy emitted from the distal end portion of said laser energy conduit can pass; and
a reflective surface at the distal end portion of said laser energy conduit situated between the laser energy conduit and the sheath for reflecting away from the sheath stray laser energy emitted from said laser energy conduit;
wherein the laser energy conduit has an outer surface, the reflective material includes inner and outer surfaces, and the sheath has an inner surface, the reflective material being sandwiched between the laser energy conduit and the sheath in a relationship wherein the outer surface of said laser energy conduit is in abutting relationship with the inner surface of said reflective material and said outer surface of said laser energy conduit is in abutting relationship with the inner surface of said sheath.

11. A laser device comprising:
a source of laser energy;
a laser energy conduit adapted for connection to the laser energy source and including a proximal end portion for coupling to the laser energy source and a distal end portion from which laser energy can be emitted;
a sheath surrounding at least part of the distal end portion of said laser energy conduit and defining a window through which laser energy emitted from the distal end portion of said laser energy conduit can pass; and
a reflective surface at the distal end portion of said laser energy conduit situated between the laser energy conduit and the sheath for reflecting away from the sheath stray laser energy emitted from said laser energy conduit;
wherein the sheath includes inner and outer surfaces and a distal endpiece defining an end face, wherein the reflective surface extends over the distal endpiece of said sheath in a relationship wherein said reflective surface covers the inner and outer surfaces as well as end face of said distal endpiece of said sheath.

12. A laser device comprising:
a source of laser energy;
a laser energy conduit adapted for connection to the laser energy source and including a proximal end portion for coupling to the laser energy source and a distal end portion from which laser energy can be emitted;
a sheath surrounding at least part of the distal end portion of said laser energy conduit and defining a window through which laser energy emitted from the distal end portion of said laser energy conduit can pass; and
a reflective surface at the distal end portion of said laser energy conduit situated between the laser energy conduit and the sheath for reflecting away from the sheath stray laser energy emitted from said laser energy conduit;
wherein said laser energy conduit comprises at least first and second abutting conduit sections, and said reflective material surrounds said laser energy conduit in the region where said first and second conduit sections are abutted together.

13. A laser device comprising:
a source of laser energy;
a laser energy conduit adapted for connection to the laser energy source and including a proximal end portion for coupling to the laser energy source and a distal end portion from which laser energy can be emitted;
a sheath surrounding at least part of the distal end portion of said laser energy conduit and defining a window through which laser energy emitted from the distal end portion of said laser energy conduit can pass; and
a reflective surface at the distal end portion of said laser enemy conduit situated between the laser energy conduit and the sheath for reflecting away from the sheath stray laser energy emitted from said laser energy conduit;
further comprising an outer plastic tube surrounding and spaced from the sheath, having a distal end adjacent to the distal end of said laser energy conductor and a proximal end defining at least one port to vent gas between the outer plastic tube and the sheath.

14. A laser device comprising
a laser energy conduit adapted for connection to a laser energy source and including a proximal end portion suitable for coupling to the laser energy source and a distal end portion from which laser energy can be emitted;

a sheath surrounding the distal end of the laser energy conduit and defining a window through which laser energy emitted from the distal end portion can pass; and a reflective surface at the distal end portion of said laser energy conduit and defined by the sheath for reflecting away from the sheath stray laser energy emitted from said laser energy conduit.

15. The laser device of claim 14 wherein the sheath terminates at the distal end thereof in a metal endpiece and the reflective surface is defined within the endpiece of the sheath.

16. A laser device comprising a laser energy conduit adapted for connection to a laser energy source and including a proximal end portion suitable for coupling to the laser energy source and a distal end portion from which laser energy can be emitted;

a sheath surrounding the distal end of the laser energy conduit and defining a window through which laser energy emitted from the distal end portion can pass; and a reflective surface at the distal end portion of said laser energy conduit and defined by the sheath for reflecting away from the sheath stray laser energy emitted from said laser energy conduit;

wherein a distal end portion of the laser energy conduit is enveloped by at least one transparent sleeve.

17. A laser device comprising a laser energy conduit adapted for connection to a laser energy source and including a proximal end portion suitable for coupling to the laser energy source and a distal end portion from which laser energy can be emitted;

a sheath surrounding the distal end of the laser energy conduit and defining a window through which laser energy emitted from the distal end portion can pass; and a reflective surface at the distal end portion of said laser energy conduit and defined by the sheath for reflecting away from the sheath stray laser energy emitted from said laser energy conduit;

wherein a distal end portion of the laser energy conduit is enveloped by a transparent open ended inner sleeve and a transparent outer sleeve having a closed distal end, the inner sleeve being concentric with the outer sleeve.

18. A laser device comprising a laser energy conduit adapted for connection to a laser energy source and including a proximal end portion suitable for coupling to the laser energy source and a distal end portion from which laser energy can be emitted;

a sheath surrounding the distal end of the laser energy conduit and defining a window through which laser energy emitted from the distal end portion can pass; and a reflective surface at the distal end portion of said laser energy conduit and defined by the sheath for reflecting away from the sheath stray laser energy emitted from said laser energy conduit;

wherein the proximal end portion of the laser energy conduit is surrounded by a transparent sleeve and the sleeve, in turn, is surrounded by a reflective material.

19. A laser device comprising a laser energy conduit adapted for connection to a laser energy source and including a proximal end portion suitable for coupling to the laser energy source and a distal end portion from which laser energy can be emitted;

a sheath surrounding the distal end portion of the laser energy conduit and defining a window through which laser energy emitted from the distal end can pass;

a reflective surface at the distal end portion of said laser energy conduit defined by the sheath for reflecting away from the sheath stray laser energy emitted from said laser energy conduit; and a closed end transparent sleeve on the distal end portion of said laser energy conduit.

20. A laser device comprising a laser energy conduit adapted for connection to a laser energy source and including a proximal end portion suitable for coupling to the laser energy source and a distal end portion from which laser energy can be emitted;

a sheath surrounding the distal end potion of the laser energy conduit and defining a window through which laser energy emitted from the distal end can pass;

reflective surface at the distal end portion of said laser energy conduit defined by the sheath for reflecting stray laser energy emitted from said laser energy conduit;

a first transparent sleeve fused to a distal end portion of said laser energy conduit; and a closed end second transparent sleeve over said first transparent sleeve and concentric therewith.

21. The laser device of claim 20 wherein said first and second transparent sleeves are made of quartz or fused silica.

22. Connector for a laser energy conduit having a proximal end portion for coupling to a source of laser energy and a distal end portion from which laser energy can be emitted, which comprises a base;

a laser energy conduit mounted to said base and having an exposed segment of optical fiber at proximal end portion thereof surrounded by said base;

a transparent sleeve surrounding said exposed segment; and a reflective material surrounding said transparent sleeve.

23. The connector of claim 22 wherein the transparent sleeve is made of quartz.

24. The connector of claim 22 wherein the transparent sleeve is made of fused silica.

* * * * *

UNITED STATES PATENT AND TRADEMARK OFFICE
CERTIFICATE OF CORRECTION

PATENT NO. : 7,492,987 B2  
APPLICATION NO. : 11/641155  
DATED : February 17, 2009  
INVENTOR(S) : Yeik et al.

Page 1 of 1

It is certified that error appears in the above-identified patent and that said Letters Patent is hereby corrected as shown below:

Column 21,
Line 3, after "portion" insert -- of --.

Column 22,
Line 54, "enemy" should be -- energy --.

Signed and Sealed this

Seventeenth Day of November, 2009

David J. Kappos
*Director of the United States Patent and Trademark Office*